US00RE45147E

(19) United States
(12) Reissued Patent
To et al.

(10) Patent Number: US RE45,147 E
(45) **Date of Reissued Patent: *Sep. 23, 2014**

(54) LENS FOR OPTICAL TREATMENT

(71) Applicant: The Hong Kong Polytechnic University, Hong Kong (CN)

(72) Inventors: Chi Ho To, Hong Kong (CN); Siu Yin Lam, Hong Kong (CN); Yan Yin Tse, Hong Kong (CN)

(73) Assignee: The Hong Kong Polytechnic University, Hong Kong (CN)

( * ) Notice: This patent is subject to a terminal disclaimer.

(21) Appl. No.: 13/662,420

(22) Filed: Oct. 27, 2012

Related U.S. Patent Documents

Reissue of:
(64) Patent No.: 7,506,983
Issued: Mar. 24, 2009
Appl. No.: 10/954,631
Filed: Sep. 30, 2004

U.S. Applications:
(63) Continuation of application No. 13/053,289, filed on Mar. 22, 2011, now Pat. No. Re. 43,851, which is an application for the reissue of Pat. No. 7,506,983.

(51) Int. Cl.
*A61B 3/00* (2006.01)

(52) U.S. Cl.
USPC ..... 351/246; 351/159; 351/168

(58) Field of Classification Search
USPC ..... 351/246, 159, 177, 161, 168, 170, 172, 351/222, 205, 202
See application file for complete search history.

(56) References Cited

U.S. PATENT DOCUMENTS

| | | | | |
|---|---|---|---|---|
| 3,904,281 | A | 9/1975 | Jampolsky | |
| 4,210,391 | A | 7/1980 | Cohen | |
| 6,045,578 | A | 4/2000 | Collins et al. | |
| 6,343,861 | B1 | 2/2002 | Kris et al. | |
| 6,491,394 | B1 * | 12/2002 | Blum et al. | 351/228 |
| 6,626,532 | B1 | 9/2003 | Nishioka et al. | |
| 7,025,460 | B2 * | 4/2006 | Smitth et al. | 351/221 |
| 2003/0058404 | A1 | 3/2003 | Thorn et al. | |
| 2003/0058407 | A1 | 3/2003 | Aller | |
| 2004/0237971 | A1 * | 12/2004 | Radhakrishnan et al. | 128/898 |
| 2005/0099597 | A1 * | 5/2005 | Sandstedt et al. | 351/168 |

FOREIGN PATENT DOCUMENTS

| | | |
|---|---|---|
| EP | 0 927 905 | 7/1999 |
| NZ | PCT/NZ2005/000155 | 1/2006 |
| RU | 2 195 233 | 12/2002 |
| RU | 2 197 198 | 1/2003 |
| WO | WO 97/10527 | 3/1997 |

OTHER PUBLICATIONS

International Search Report and Written Opinion of the International Searching Authority, dated Jan. 5, 2006, prepared by The International Searching Authority/China.

(Continued)

*Primary Examiner* — Dawayne A Pinkney

(57) ABSTRACT

A method for treating progression of a refractive disorder in a human eye. The method includes the steps of producing a first image on a retina of the human eye and producing a second image to generate a defocus.

7 Claims, 13 Drawing Sheets

(56) References Cited

OTHER PUBLICATIONS

Diether, Sigrid and Frank Schaeffel, "Local Changes in Eye Growth induced by Imposed Local Refractive Error despite Active Accommodation", Vision Research, 1997 vol. 37, No. 6, pp. 659-668 (Elsevier Science Ltd., Great Britain).

Edwards, Marion Hastings, et al., "The Hong Kong Progressive Lens Myopia Control Study: Study Design and Main Findings", Investigative Ophthalmology & Visual Science, Sep. 2002, vol. 43, No. 9, pp. 2852-2858 (Association for Research in Vision and Ophthalmology).

Gwiazda, Jane, et al., "A Randomized Clinical Trial of Progressive Addition Lenses versus Single Vision Lenses on the Progression of Myopia in Children", Investigative Ophthalmology & Visual Science, Apr. 2003 vol. 44, No. 4, pp. 1492-1500 (Association for Research in Vision and Ophthalmology).

Kee, C.S. et al., "The Role of Peripheral Vision in the Refractive Vision in the Refractive-Error Development of Infant Monkeys (*Macaca mulatta*)", Investigative Ophthalmology and Visual Science, 2004; vol. 45, E-Abstract 1157 (Association for Research in Vision and Ophthalmology).

Schaeffel, Frank and Sigrid Diether, "The growing eye: an autofocus system that works on very poor images", Vision Research, 1999, vol. 39, pp. 1585-1589 (Elsevier Science Ltd.).

Shaikh, Adam W. et al., "Effect of Interrupted Lens Wear on Compensation for a Minus Lens in Tree Shrews", Optometry and Vision Science, May 1999, vol. 76, No. 5, pp. 308-315 (American Academy of Optometry).

Smith, Earl L. III and Li-Fang Hung, "The role of optical defocus in regulating refractive development in infant monkeys", Vision Research, 1999, vol. 39, pp. 1415-1435 (Elsevier Science Ltd.).

Troilo, David and Josh Wallman, "The Regulation of Eye Growth and Refractive State: An Experimental Study of Emmetropization", Vision Research, 1991, vol. 31, pp. 1237-1250 (Pergamon Press plc).

Wallman, Josh, "Temporal and spatial aspects of visual guidance of eye growth", Proceedings of the 10$^{th}$ International Myopia Conference, edited by Daniel J.O. Leary and Hema Radhakrishnan, 2004, pp. 18 (APU, Cambridge, UK, ISBN: 0-907262-67-8).

Wallman, Josh and Jonathan Winawer, "Homeostasis of Eye Growth and the Question of Myopia", Neuron, Aug. 19, 2004, vol. 43, pp. 447-468 (Cell Press).

Zhong, Zingwu et al., "Compensation for experimentally induced hyperopic anisometropia in adolescent monkeys", Investigative Ophthalmology & Visual Sciene, Oct. 2004, vol. 45, No. 10, pp. 3373-3379 (Association for Research in vision and Ophthalmology).

* cited by examiner

LENS FOR OPTICAL TREATMENT

Matter enclosed in heavy brackets [ ] appears in the original patent but forms no part of this reissue specification; matter printed in italics indicates the additions made by reissue.

*CROSS REFERENCE TO RELATED APPLICATIONS*

*Notice: More than one reissue application has been filed of the reissue of U.S. Pat. No. 7,506,983. The reissue applications are application Ser. Nos. 13/662,420 (the present application) and 13/053,289.*

*This application is a continuation reissue application of application Ser. No. 13/053,289 (now U.S. Pat. No. Re. 43,851), which is an application for reissue of U.S. Pat. No. 7,506,983.*

FIELD OF THE INVENTION

The present invention relates to a method of optical treatment. In particular, the present invention relates to a method for treating progression of refractive disorders, such as myopia and hyperopia, in human eyes.

BACKGROUND OF THE INVENTION

The retina is the innermost layer of an eyeball and is the place where optical images created by the lens of the eye is focused. The information from the images are turned into nerve impulses, which are then sent to the brain via the optic nerve. If the retina does not coincide with the resultant focal point of the optical elements of the eye, defocus is generated. As used herein, the term "defocus" refers to the shift of the optical images to a point behind or in front of the retina. The human eye has a feedback mechanism that regulates the growth of the eye to achieve an optimal balance between the size/length of the eye and the focal length of the optical elements of the eye. This feedback mechanism is called emmetropization.

Myopia and hyperopia are common refractive disorders of human eyes. They are generally described as an imbalance between the focusing power of optical elements of the eye and the size/length of the eye. Focus of a myopic eye lies in front of the retina of the eye, while focus of a hyperopic eye lies behind the retina of the eye. It is generally accepted that these disorders are results of inaccurate axial growth during post-natal development of the eyes. In other words, myopia typically develops when the size/length of the eye grows to exceed the focal length of the optical elements of the eye, while hyperopia typically develops when the size/length of the eye grows to be shorter than the focal length of the optical elements of the eye.

Referring to FIG. 1, an optical image 12 is formed in front of the retina in the case of myopia. Defocus in this case is positive and called myopic defocus 13. The emmetropization mechanism operates to retard eye growth in size until the retina 11 coincides with the optical image 12 when the myopic defocus 13 diminished. As a result, the eye becomes less myopic.

Referring to FIG. 2, optical image 22 is formed behind the retina 21 in the case of hyperopia. Defocus in this form is negative and called hyperopic defocus 23. The emmetropization mechanism operates to promote eye growth in size until the retina 21 coincides with the optical image 22 when the hyperopic defocus 23 diminished. As a result, the eye becomes less hyperopic.

Referring to FIG. 3, the natural major sources of defocus for a human eye come from accommodation lag and ambient defocus. The accommodation lag is generally projected by the object of interest 35 onto the center of the retina 31 or macula 34 along a visual axis 32. It usually ranges from 0.5 D to 1.0 D of hyperopic defocus 36 for a non-presbyope during near visual tasks, such as reading. Ambient defocus is projected by peripheral visual objects other than the object of interest 35. Since peripheral objects are usually positioned more distant than the object of interest 35, they usually produce myopic defocus up to 3.0 D during near visual tasks. For example, peripheral object 37 produce myopic defocus 38 at periphery of retina 31. Habitually, the peripheral visual objects are seldom positioned closer than the object of interest 35. However, if they do like peripheral object 39, hyperopic defocus 33 will be produced.

The natural process of emmetropization is regulated by the equilibrium between the above opposite defocus. Incidences of refractive errors are secondary to the disruption of the equilibrium. For example, insufficient ambient myopic defocus may cause myopia. On the other hand, excessive ambient myopic defocus may cause hyperopia.

Existing optical aids and refractive surgeries, in the form of spectacles, contact lens, corneal implant or shape modification of cornea, are corrective approaches involving alteration of the gross focusing power of the eye to produce sharper retinal images. They do not eliminate or deal with the cause of the disorders, but are just prosthetic.

The existing optical treatments to retard the progression of myopia by relieving the eye's accommodation during near visual tasks are recently shown to be clinically ineffective. Examples of those treatments include bi-focal addition lenses, multi-focal progressive addition lenses and their derivatives, and spherical aberration manipulations.

SUMMARY OF THE INVENTION

The present invention is directed to a method for treating progression of a refractive disorder in a human eye. Particularly, the present invention provides methods for counteracting the development of myopia by enhancing myopic defocus. The present invention also provides methods for counteracting the development of hyperopia by enhancing hyperopic defocus. The apparatuses used in practice of the present invention alter the defocus equilibrium of the eye to influence axial eye growth in a direction towards emmetropia.

According to a general aspect of the present invention, the method for treating progression of a refractive disorder in a human eye includes producing a first image on a retina of the human eye and producing a second image to generate a defocus.

According to one aspect of the present invention, the method for treating progression of a refractive disorder in a human eye includes providing a Fresnel lens having primary optical zones and secondary optical zones. The primary optical zones include a primary refractive power, and secondary optical zone includes at least one secondary refractive power. The method also includes correcting the refractive disorder with the primary refractive power and generating at least one defocus with the secondary refractive power.

According to another aspect of the present invention, the method for treating progression of a refractive disorder in a human eye includes prescribing an optical system having a back layer and a partially transparent front layer. The method also includes producing a primary image of one of the front and back layers on a retina of the human eye and producing a secondary image of the other layer of the front and back layers to generate a defocus.

According to yet another aspect of the present invention, the method for treating progression of a refractive disorder in a human eye includes providing a lens including a central optical zone having a primary optical power and at least one peripheral optical zone having a secondary optical power. The method also includes producing a primary image on a retina of the human eye with the first optical power and producing at least one secondary image with the second optical power to generate a defocus.

According to yet another aspect of the present invention, the method for treating progression of a refractive disorder in a human eye includes prescribing an optical system having a central visual object and at least one peripheral visual object. The method also includes producing a first image of the central visual object on a central retina of the human eye and producing a second image of the peripheral visual object to generate a defocus.

BRIEF DESCRIPTION OF THE DRAWINGS

FIG. 4b is a back view of the Fresnel type concentric bi-focal or multi-focal lens of FIG. 4a.

FIG. 8b is a back view of the central-peripheral multi-focal lens of FIG. 8a.

DETAILED DESCRIPTION OF THE INVENTION

The present invention is directed to a method for treating progression of a refractive disorder in a human eye. Particularly, the present invention provides a method for counteracting the development of myopia by enhancing myopic defocus. The present invention also provides a method for counteracting the development of hyperopia by enhancing of hyperopic defocus. The apparatuses used in practice of the present invention alter the defocus equilibrium of the eye to influence axial eye growth in a direction towards emmetropia.

The artificial shift of the defocus equilibrium in the optical system of the eye may be introduced by any desired method, for example by spectacle lens, spectacle lens add-on, contact lens, corneal shape-modification, ocular implant or designated viewing system. It is preferred that the shift be introduced together with the conventional correction so that normal vision can be maintained throughout the treatment. This means that a focused image must be maintained near the macula 34, while one or more defocused images are being introduced into the optical system of the eye.

A treatment method in accordance with the present invention introduces at least a defocused image and a focused image in a superimposed manner. The defocused and focused images can be introduced simultaneously, for example, by a concentric Fresnel type bi-focal or multi-focal lens as shown in FIGS. 4-6, diffractive multi-focal lens and their derivatives, or an optical system as shown in FIG. 7.

Figure 1:
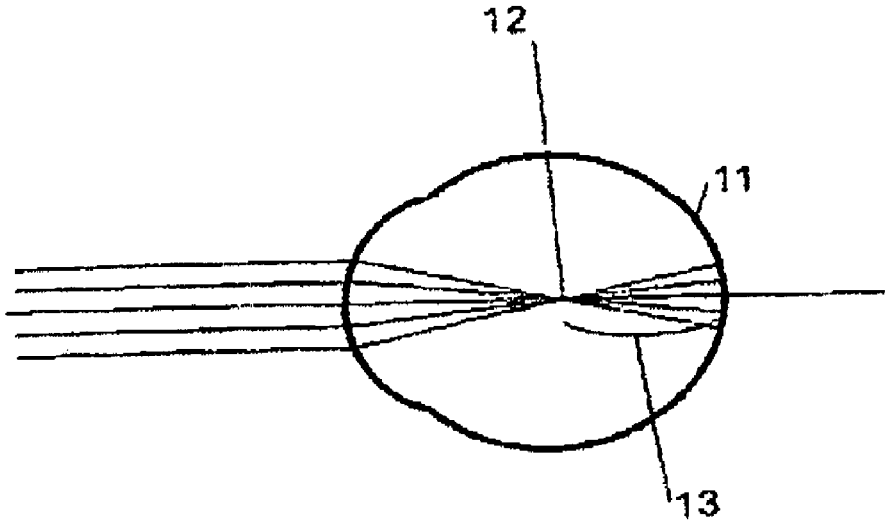
FIG. 1 PRIOR ART
FIG. 1 is a schematic diagram showing the section of a myopic eye and the nature of myopic defocus.
Figure 2:
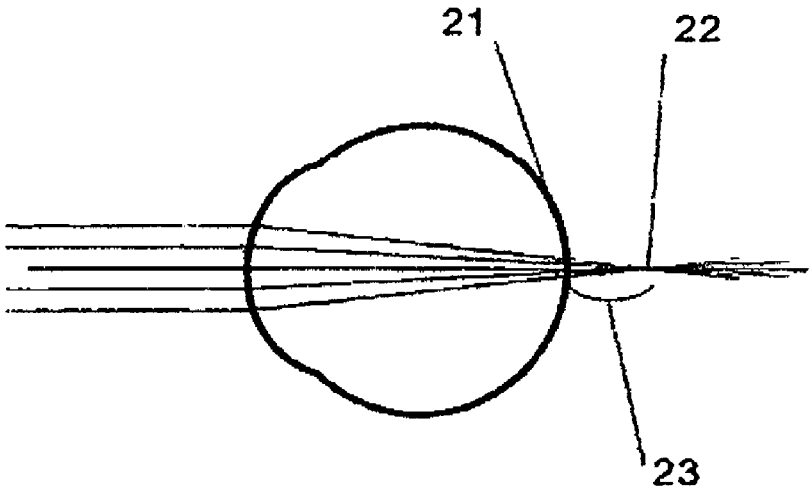
FIG.2 PRIOR ART
FIG. 2 is a schematic diagram showing the section of a hyperopic eye and the nature of hyperopic defocus.
Figure 3:
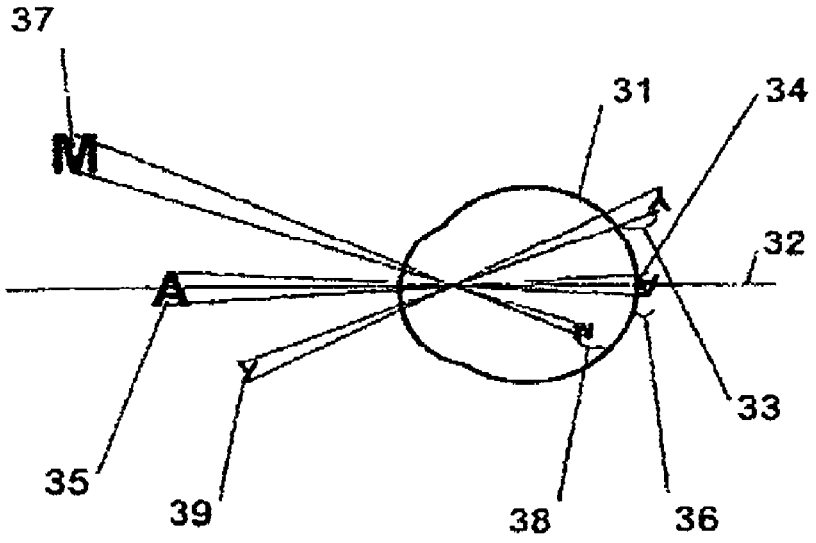
FIG.3 PRIOR ART
FIG. 3 is schematic diagram showing the section of an eye, illustrating the source and the formation of accommodation lag and ambient defocus.
Figure 4A:
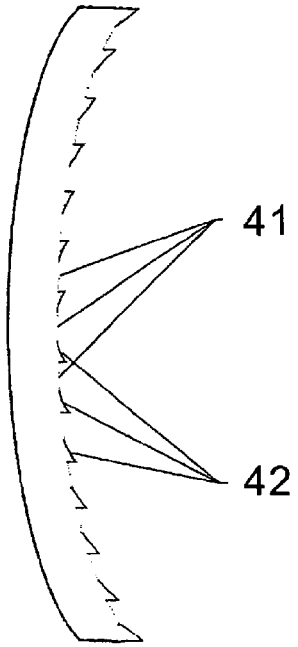
FIG. 4a is a cross-sectional view of a Fresnel type concentric bi-focal or multi-focal lens used in practice of the present invention.
Figure 4B:
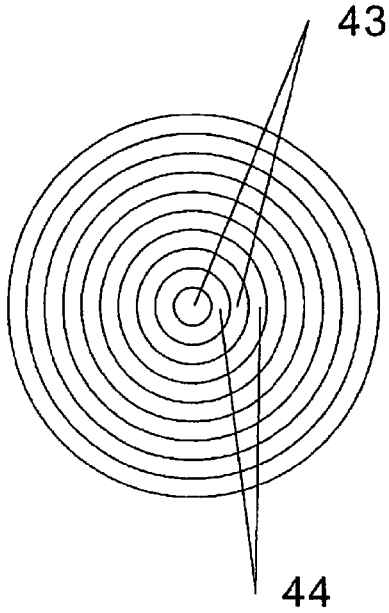

Referring now FIGS. 4a and 4b, there shown is the Fresnel concentric bi-focal or multi-focal lens having alternating concentric optic zones 41 and 42 of at least two refractive powers used in practice of the present invention. A common way to manufacture the Fresnel concentric bi-focal lens is to make one of the surfaces with two radius of curvature. For example, the zone 42 with a shorter radius of curvature (i.e. more curved) than the other zone 41 with a longer radius of curvature (i.e. flatter) exhibits a more negative refractive power. The zone with a more negative power 44 and the zone with a less negative power 43 alternate in a concentric manner. As a result, paraxial light rays and peripheral light rays share two common focal points.

Figure 5A:
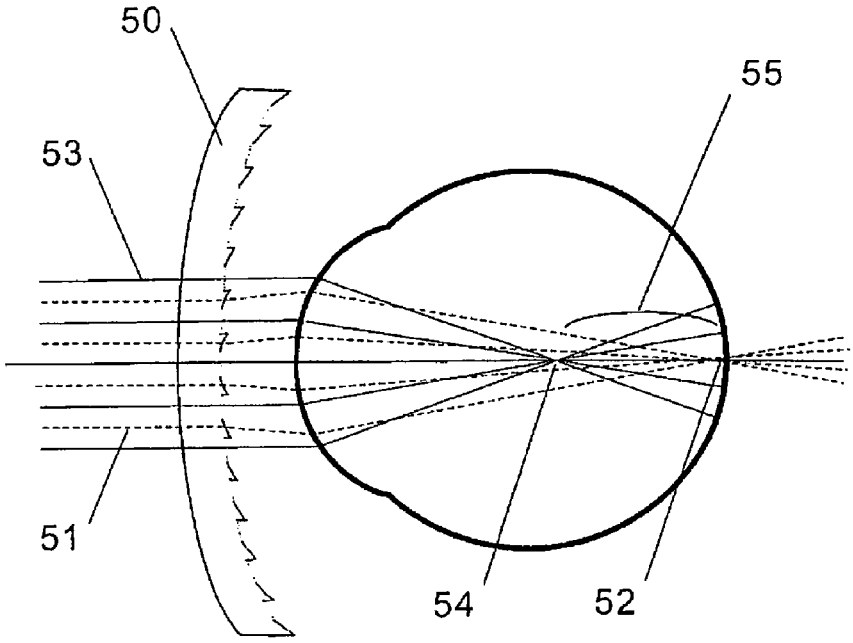
FIG. 5a is a diagram of a myopic eye fitted with a concentric bi-focal lens in accordance with the present invention.

FIG. 5a shows a myopic eye fitted with a Fresnel type concentric bi-focal lens 50 having a primary refractive power correcting the myopia and a secondary power to introduce myopic defocus in accordance with the present invention. Light rays 51 entering the optical zones having the primary power are focused on the retina 52, producing a sharp image of a visual object. At the same time, other light rays 53 entering the optical zones having the secondary power are focused at a point 54 in front of the retina 52, producing the myopic defocus 55. When a myopic patient uses the lens 50 to view an object, the myopic defocus 55 prevents the eye from growing or elongating. Consequently, myopic progression in the myopic eye is slowed, stopped or reversed.

Figure 6A:
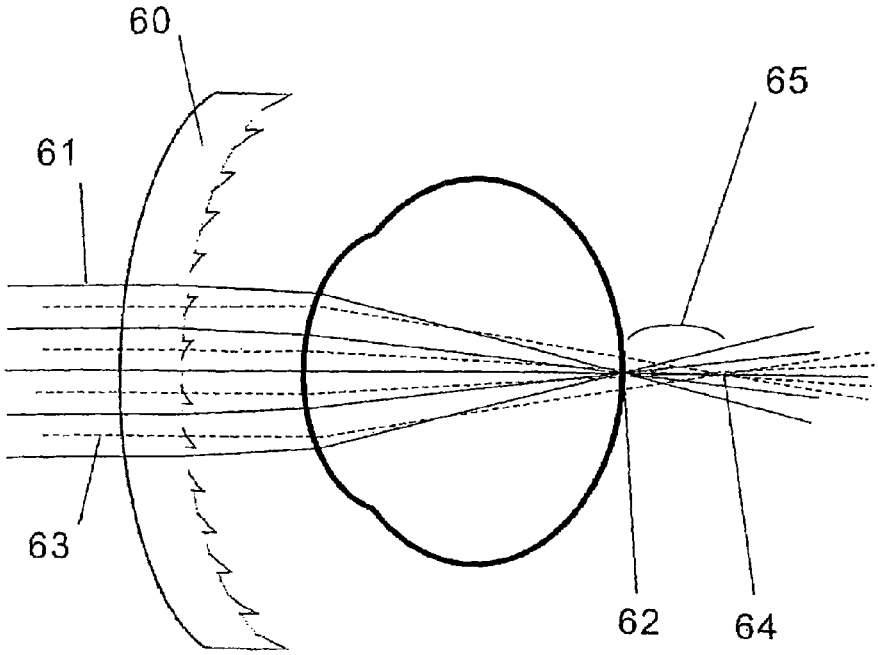
FIG. 6a is a diagram of a hyperopic eye fitted with a concentric bi-focal lens in accordance with the present invention.

FIG. 6a shows a hyperopic eye fitted with a Fresnel type concentric bi-focal lens 60 having a primary refractive power to correct the hyperopia and a secondary power to introduce hyperopic defocus. Light rays 61 entering the optical zones having the primary power are focused onto the retina 62, producing a sharp image of a visual object. Simultaneously, other light rays 63 entering the optical zones having the secondary power are focused at a point 64 behind the retina 62, producing the hyperopic defocus 65. When a hyperopic patient uses the lens 60 to view an object, the hyperopic defocus 65 promotes the eye in growing or elongating. Consequently, myopic progression in the hyperopic eye is increased or induced, and hyperopia is reduced.

A Fresnel type of concentric multi-focal lens is a derivative of the Fresnel type concentric bi-focal lens. It has alternating concentric optic zones of more than two refractive powers. The primary refractive power corrects the refractive error, while the multiple secondary powers introduce optical defocus for treatment. This can be achieved by a minor variation on the radius of curvature of the secondary optical zones.

Figure 5B:
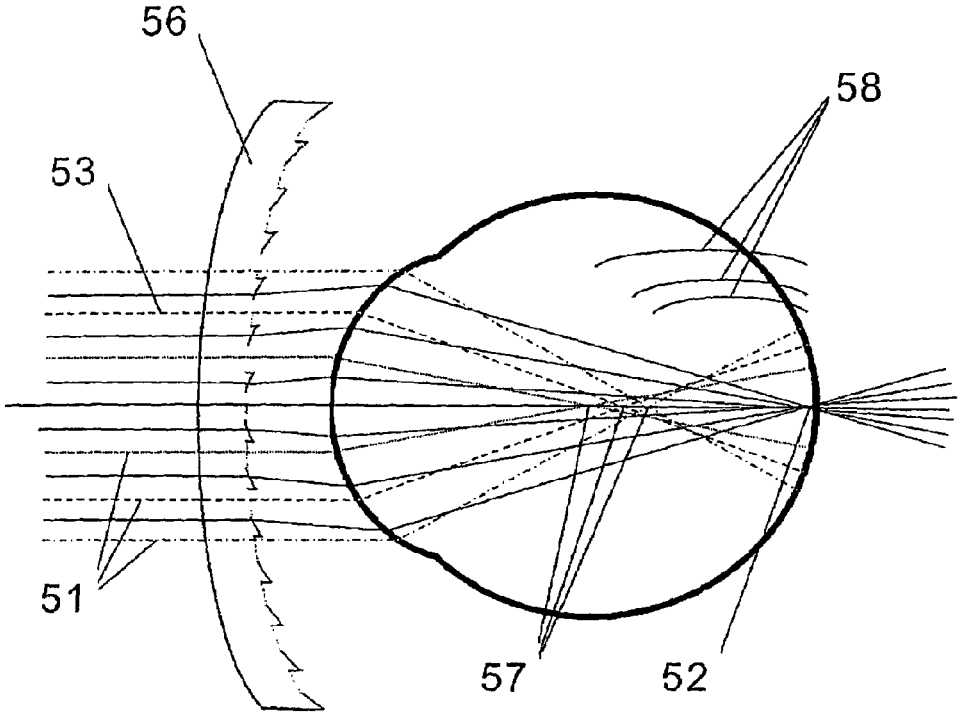
FIG. 5b is a diagram of a myopic eye fitted with a concentric multi-focal lens in accordance with the present invention.

FIG. 5b shows a myopic eye fitted with a Fresnel type concentric multi-focal lens 56 in accordance with the present invention. Light rays 51 entering the optical zones having the primary power are focused on the retina 52, producing a sharp image of a visual object. At the same time, other light rays 53 entering the optical zones having the secondary powers are focused at points 57 in front of the retina 52, producing multiple myopic defocus 58 of various amplitudes. When a myopic patient uses the lens 56 to view an object, the myopic defocus 58 prevent the eye from growing or elongating. Consequently, myopic progression in the myopic eye is slowed, stopped or reversed.

Figure 6B:
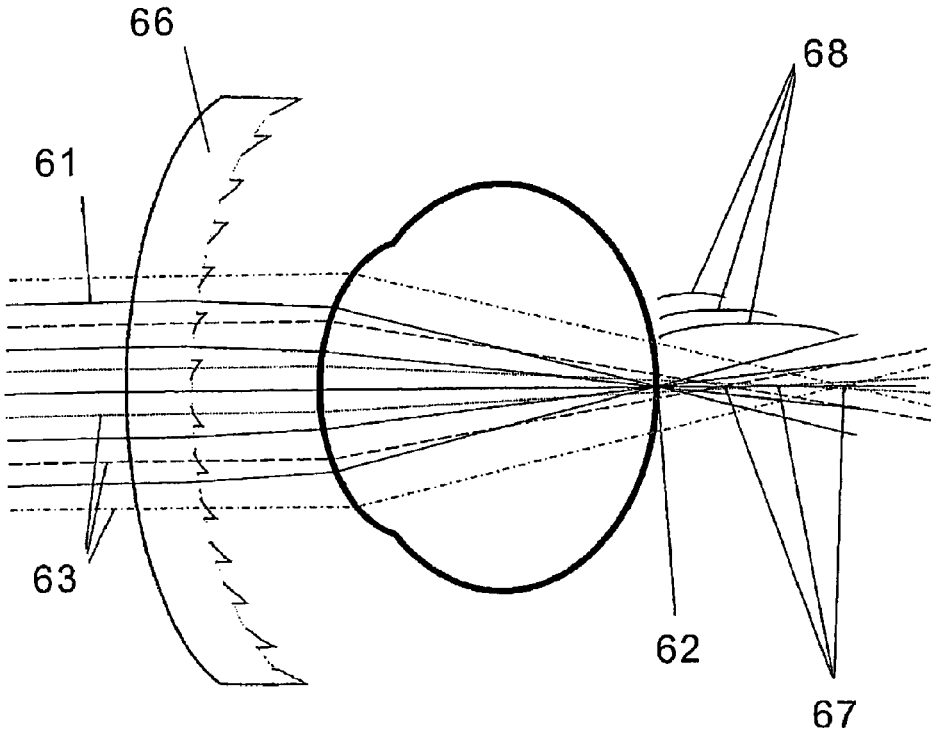
FIG. 6b is a diagram of a hyperopic eye fitted with a concentric multi-focal lens in accordance with the present invention.

FIG. 6b shows a hyperopic eye fitted with a Fresnel type concentric multi-focal lens 66. Light rays 61 entering the optical zones having the primary power are focused onto the retina 62, producing a sharp image of a visual object. Simultaneously, other light rays 63 entering the optical zones having the secondary powers are focused at points 67 behind the retina 62, producing multiple hyperopic defocus 68 of various amplitudes. When a hyperopic patient uses the lens 66 to view an object, the hyperopic defocus 68 promotes the eye in growing or elongating. Consequently, myopic progression in the hyperopic eye is increased or induced, and hyperopia is reduced.

Figure 7A:
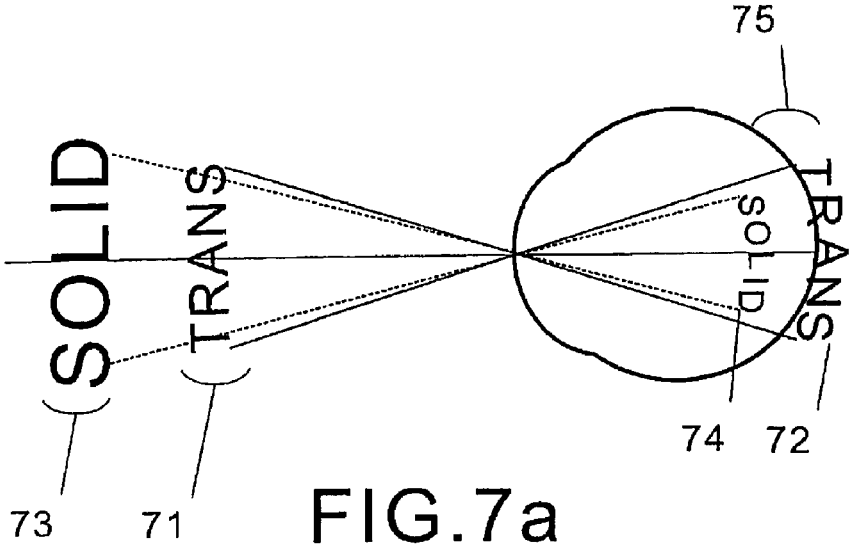
FIG. 7a is a diagram of a myopic eye fitted with an optical system having of a semi-transparent front layer and a non-transparent back layer in accordance with the present invention.

FIG. 7a shows a myopic eye fitted with an optical system having a primary semi-transparent front layer 71 and a secondary non-transparent back layer 73 in accordance with the present invention. The front layer 71 matches the focal point of the eye, producing a sharp image 72 on the retina. At the same time, the back layer 73 produces an image 74 in front of the retina causing a myopic defocus 75 superimposed on the sharp image 72. When a myopic patient uses this optical system, the myopic defocus 75 prevents the eye from growing or elongating. Consequently, myopic progression in the myopic eye is slowed, stopped or reversed.

Figure 7B:
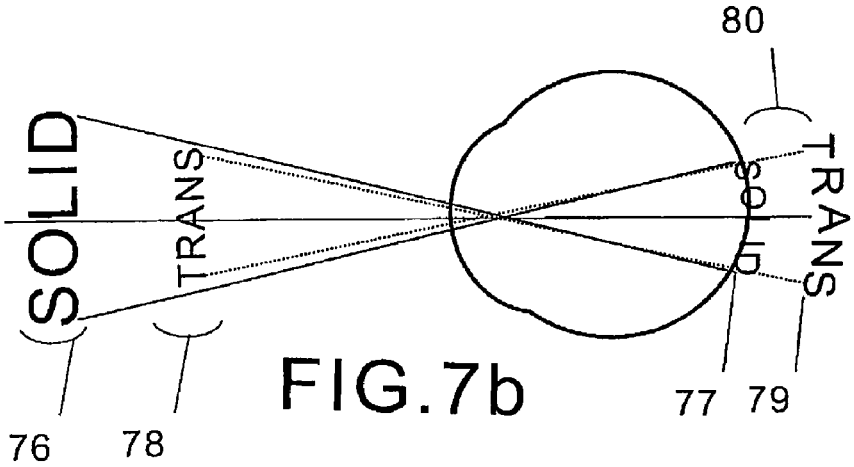
FIG. 7b is a diagram of a hyperopic eye fitted with an optical system having a non-transparent back layer and a semi-transparent front layer in accordance with the present invention.

FIG. 7b shows a hyperopic eye fitted with an optical system having a primary non-transparent back layer 76 and a secondary semi-transparent front layer 78 in accordance with the present invention. The back layer 76 matches the focal point of the eye, producing a sharp image 77. In the same time, the front layer 78 produces an image 79 behind the retina causing a hyperopic defocus 80 superimposed on the sharp image 77. When a hyperopic patient uses this optical system, the hyperopic defocus 80 promotes the eye in growing or elongating. Consequently, myopic progression in the hyperopic eye is increased or induced, and hyperopia is reduced.

To improve the visual performance produced by the treatment methods and to avoid the user from mixing up his or her primary and secondary optical components, the optical quality of the retinal image produced by the primary components can be strengthened over the image produced by the secondary components. This can be achieved by manipulating the area ratio between the different zones of the Fresnel lenses and manipulating the transmission proportion of the semi-transparent layers.

An alternative method in accordance with the present invention introduces defocused image at peripheral retina only and keeps focused image at central retina. People habitually maintain a sharp image at central retina by a voluntary fixation reflex. Accordingly, the way to simultaneously present two images is the introduction of the defocus image at peripheral retina through the use of a central-peripheral multi-focal lens as shown in FIGS. 8-10 and a optical system as shown in FIG. 11.

Figure 8A:
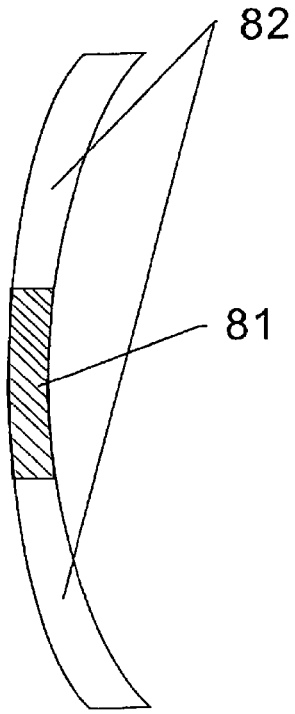
FIG. 8a is a cross-sectional view of a central-peripheral multi-focal lens used in practice of the present invention.
Figure 8B:
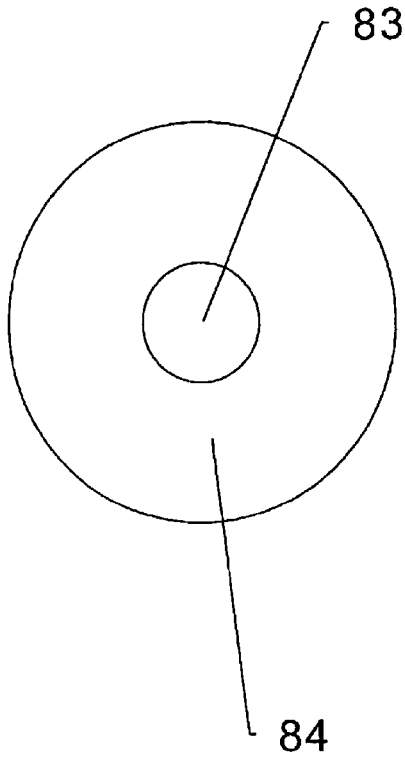

As shown in FIGS. 8a and 8b, the central-peripheral multi-focal lens includes concentric optical zones of two or more optical powers. One way to manufacture this kind of lens is to generate the zones with materials of different refractive index. The central zone 81, which has a higher refractive index than the peripheral zone 82, exhibits higher refractive power. The two zones 81 and 82 are positioned in a generally concentric manner, with the refractive power decreasing from the central towards the peripheral across the lens. The transition can be subtle or progressive, depending on the manufacturing process.

Figure 9:
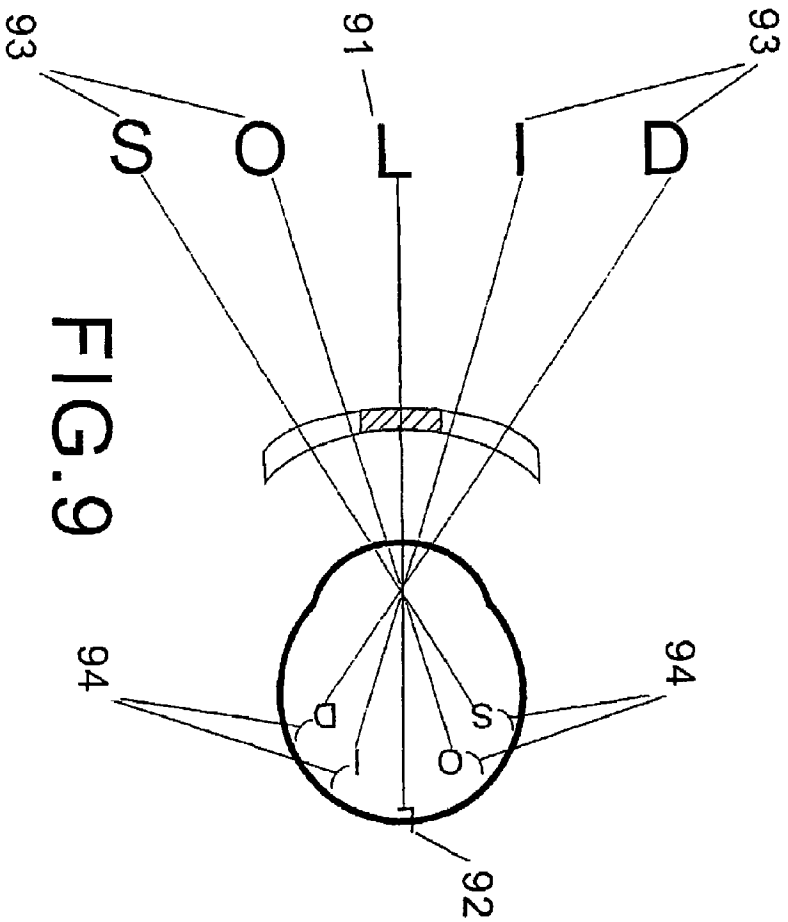
FIG. 9 is a diagram of a myopic eye fitted with the central-peripheral multi-focal lens of FIG. 8a and FIG. 8b in accordance with the present invention.

FIG. 9 shows a myopic eye fitted with a negative central-peripheral multi-focal lens, which has a primary central refractive power correcting the myopia and a secondary peripheral refractive power to introduce myopic defocus, in accordance with the present invention. Light rays entering the central zone of the lens from a central visual objects 91 are focused onto the central retina, producing a corresponding central sharp image 92. Simultaneously, light rays entering the peripheral zone of the lens from the peripheral visual objects 93 are focused at points in front of the peripheral retina, producing the peripheral myopic defocus 94 required for the treatment effect for myopia. When a myopic patient uses the lens to view the visual objects 91 and 93, the myopic defocus 94 prevents the eye from growing or elongating. Consequently, myopic progression in the myopic eye is slowed, stopped or reversed.

Figure 10:
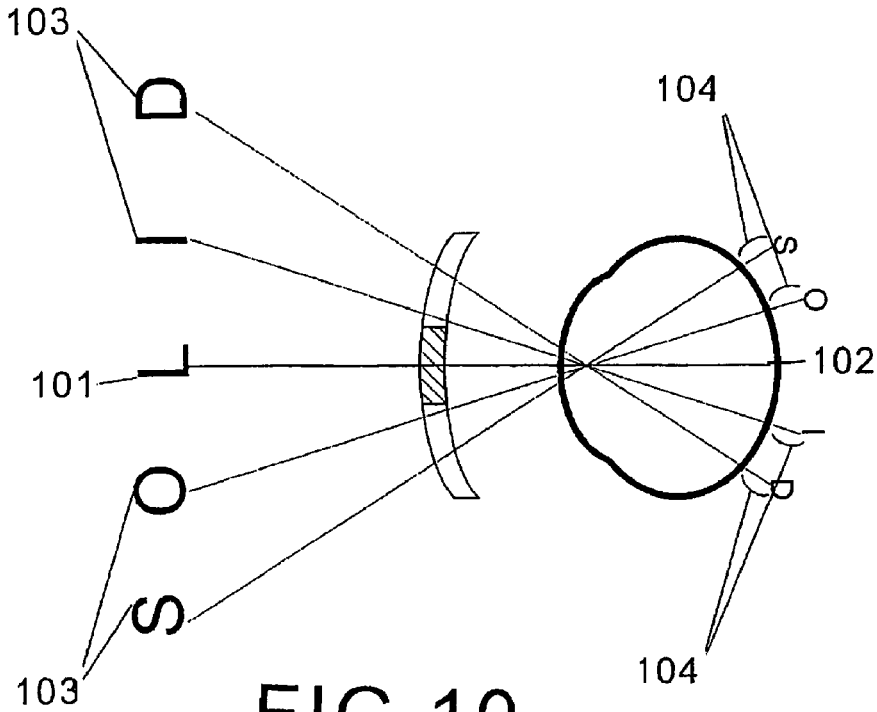
FIG. 10 is a diagram of a hyperopic eye fitted with the central-peripheral multi-focal lens of FIG. 8a and FIG. 8b in accordance with the present invention.

FIG. 10 shows a hyperopic eye fitted with a positive central-peripheral multi-focal lens, which have a primary central refractive power correcting the hyperopia and a secondary peripheral refractive power to introduce hyperopic defocus, in accordance with the present invention. Light rays entering the central zone of the lens from the central visual objects 101 are focused onto the central retina, producing a corresponding central sharp image 102. Simultaneously, light rays entering the peripheral zone of the lens from the peripheral visual objects 103 are focused at points behind the peripheral retina, producing the peripheral hyperopic defocus 104 required for the treatment effect for hyperopia. When a hyperopic patient uses this optical system, the hyperopic defocus 104 promotes the eye in growing or elongating. Consequently, myopic progression in the hyperopic eye is increased or induced, and hyperopia is reduced.

Figure 11A:
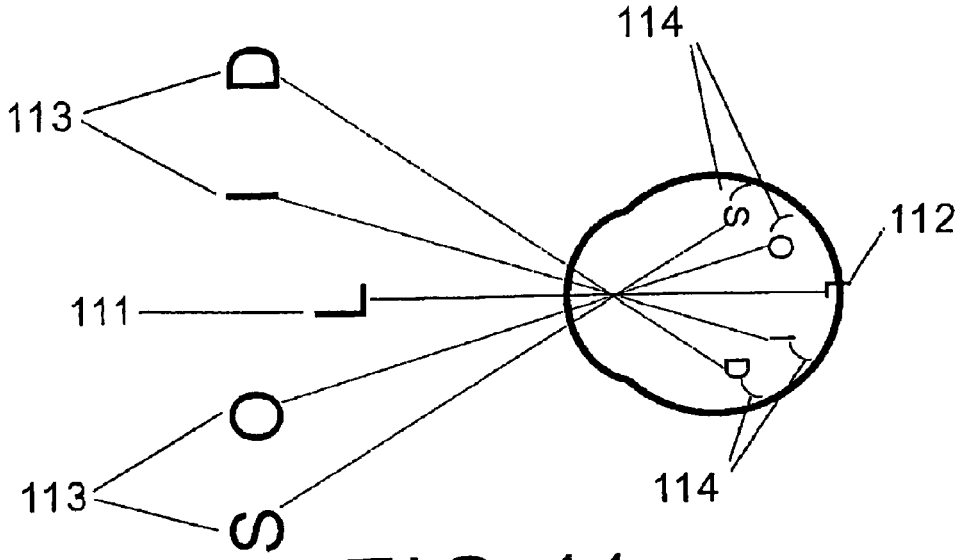
FIG. 11a is a diagram of a myopic eye fitted with an optical system having peripheral visual objects positioned closer than a central visual object in accordance with the present invention.

FIG. 11a shows a myopic eye fitted with a pre-designed visual environment or an optical system, which has peripheral visual objects 113 positioned far away from the eye compared with the central visual object 111, in accordance with the present invention. Light rays from the central object 111, as directed by basic optics and the fixation reflex of the eye, are focused onto the central retina, producing a corresponding central sharp image 112. Simultaneously, light rays from peripheral visual objects 113 are focused at points in front of the peripheral retina, producing peripheral myopic defocus 114 required for the treatment of myopia. When a myopic patient uses this optical system, the myopic defocus 114 prevents the eye from growing or elongating. Consequently, myopic progression in the myopic eye is slowed, stopped or reversed.

Figure 11B:
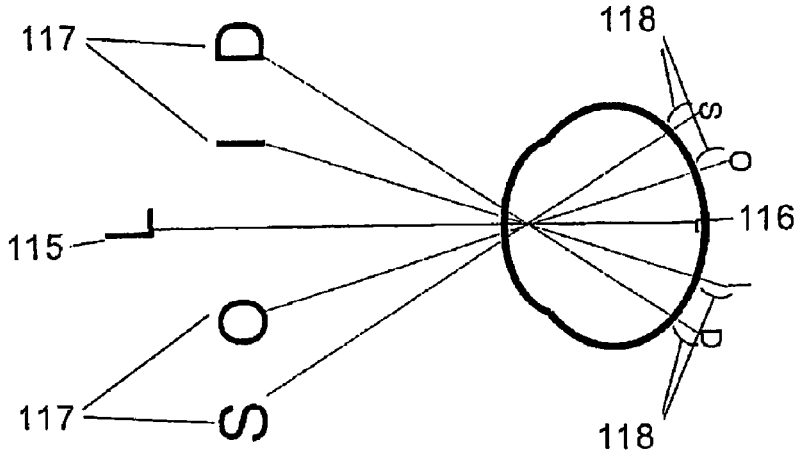
FIG. 11b is a diagram of a hyperopic eye fitted with an optical system having peripheral visual objects positioned closer than a central visual object in accordance with the present invention.

FIG. 11b shows a hyperopic eye fitted with a pre-designed visual environment or an optical system, which has peripheral visual objects 117 positioned close to the eye compared with the central visual object 115. Light rays from the central object 115, as directed by basic optics and the fixation reflex of the eye, are focused onto the central retina producing a corresponding central sharp image 116. Simultaneously, light rays from peripheral visual objects 117 are focused at points behind the peripheral retina, producing peripheral hyperopic defocus 118 required for the treatment of hyperopia. When a hyperopic patient uses this optical system, the hyperopic defocus 118 promotes the eye in growing or elongating. Consequently, myopic progression in the hyperopic eye is increased or induced, and hyperopia is reduced.

Although the present invention has particular applications in curing and preventing the progression of refractive disorders of the eye such as myopia and hyperopia, it is to be understood that the invention could be used in other applications such as the prevention of pathological myopic degeneration of the eye.

Although the present invention has been described with reference to preferred methods, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

We claim:

[1. A method for retarding the progression of myopia or hyperopia in a human eye, the method comprising:

(a) providing a Fresnel concentric multi-focal lens comprising primary optical zones having a primary refractive power and secondary optical zones having at least one secondary refractive power; and (b) correcting the myopia or hyperopia with the primary refractive power and generating at least one defocus with the secondary refractive power, wherein the primary optical zones enable near and distant objects to be viewed; and the secondary optical zones generate myopic defocus to retard myopia or generate hyperopic defocus to retard hyperopia.]

[2. The method of claim 1, wherein:

the step (b) comprises focusing a first stream of light rays of an object onto a retina of the human eye through the primary optical zones to correct the myopia and focusing a second stream of light rays of the object in front of the retina through the secondary optical zones to generate at least one myopic defocus.]

[3. The method of claim 1, wherein:

the step (b) comprises focusing a primary stream of light rays of an object onto a retina of the human eye through the first optical zones to correct the hyperopia and focusing a second stream of light rays of the object behind the retina through the secondary optical zones to generate at least one hyperopic defocus.]

[4. The method of claim 1, wherein the step (a) comprises prescribing a Fresnel concentric bi-focal lens to produce a defocus in step (b).]

[5. The method of claim 1, wherein the step (a) comprises providing a Fresnel concentric multi-focal lens producing two or more defocuses in step (b).]

[6. The method of claim 1, wherein the Fresnel concentric multi-focal lens is a concentric bi-focal lens.]

*7. A Fresnel concentric multi-focus lens for retarding the progression of myopia or hyperopia in a human eye, the lens comprising:*

*(a) primary optical zones having a primary refractive power, wherein the primary refractive power corrects the myopia or hyperopia; and*

*(b) secondary optical zones having at least one secondary refractive power, wherein the secondary refractive power generates at least one defocus,*

*wherein the primary optical zones enable near and distant objects to be viewed; and the secondary optical zones generate myopic defocus to retard myopia or generate hyperopic defocus to retard hyperopia.*

*8. The lens of claim 7, wherein:*

*the primary optical zones focus a first stream of light rays of an object onto a retina of the human eye to correct the myopia, and the secondary optical zones focus a second stream of light rays of the object in front of the retina to generate at least one myopic defocus.*

*9. The lens of claim 7, wherein:*

*the primary optical zones focus a first stream of light rays of an object onto a retina of the human eye to correct the hyperopia, and the secondary optical zones focus a second stream of light rays of the object behind the retina to generate at least one hyperopic defocus.*

*10. The lens of claim 7, wherein the Fresnel concentric multi-focal lens is a bi-focal lens that produces a single defocus.*

*11. The lens of claim 7, wherein the Fresnel concentric multi-focal lens produces two or more defocuses.*

*12. The lens of claim 7, wherein the primary optical zones are configured for generating a focused image in a central optic zone, and the secondary optical zones are configured for generating a defocused image in the central optic zone at a spaced distance from the focused image.*

*13. The lens of claim 7, wherein the lens is a contact lens.*

* * * * *